United States Patent [19]
Frisch et al.

[11] Patent Number: 5,700,472
[45] Date of Patent: Dec. 23, 1997

[54] OIL-IN-WATER EMULSIONS

[75] Inventors: Gerhard Frisch, Wehrheim; Zoltan Damo, Eppstein, both of Germany

[73] Assignee: Hoechst Aktiengesellschaft, Germany

[21] Appl. No.: 436,246

[22] PCT Filed: Nov. 11, 1993

[86] PCT No.: PCT/EP93/03165

§ 371 Date: May 17, 1995

§ 102(e) Date: May 17, 1995

[87] PCT Pub. No.: WO94/10839

PCT Pub. Date: May 26, 1994

[30] Foreign Application Priority Data

Nov. 18, 1992 [DE] Germany ............ 42 38 865.1

[51] Int. Cl.$^6$ ............ A61K 9/107; A01N 25/04
[52] U.S. Cl. ............ 424/405; 424/400; 514/938; 514/941
[58] Field of Search ............ 424/405, 400; 514/938, 941

[56] References Cited

U.S. PATENT DOCUMENTS

| | | |
|---|---|---|
| 3,317,305 | 5/1967 | Stefcik et al. |
| 4,107,302 | 8/1978 | Watanable |
| 4,500,348 | 2/1985 | Hausmann et al. |
| 4,770,694 | 9/1988 | Iwasaki et al. |
| 4,851,421 | 7/1989 | Iwasaki et al. ............ 424/405 |
| 4,870,103 | 9/1989 | Röechling et al. |

FOREIGN PATENT DOCUMENTS

| | | |
|---|---|---|
| 0597314 | 6/1987 | Australia |
| 0629914 | 9/1990 | Australia |
| 0645136 | 7/1964 | Belgium |
| 2031322 | 6/1991 | Canada |
| 0062181 | 10/1982 | European Pat. Off. |
| 0130370 | 1/1985 | European Pat. Off. |
| 0190995 | 8/1986 | European Pat. Off. |
| 0224846 | 6/1987 | European Pat. Off. |
| 0257286 | 3/1988 | European Pat. Off. |
| 0432062 | 6/1991 | European Pat. Off. |
| 3210869 | 10/1982 | Germany |
| WO 90/09103 | 8/1990 | WIPO |

*Primary Examiner*—Thurman K. Page
*Attorney, Agent, or Firm*—Connolly & Hutz

[57] ABSTRACT

The present invention relates to oil-in-water emulsions comprising 0.001–70% by weight, preferably from 0.5 to 45% by weight, of at least one active substance from the class of the phosphates and/or carbamates, from 0.001–20% by weight, preferably from 0.1–10% by weight, of at least one salt of an aryl polyglycol ether phosphate of the formula I

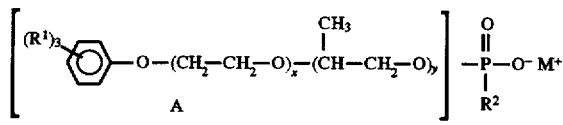

in which
each $R^1$, independently of the others, is hydrogen, $C_1$–$C_{24}$-alkyl, $C_5$–$C_{15}$-cycloalkyl, $C_8$–$C_{24}$-aryl or $C_6$–$C_{24}$-alkaryl, $R^2$ is hydrogen, —O—$C_1$–$C_{24}$-alkyl, —O—$C_5$–$C_{15}$-cycloalkyl, —O—$C_6$–$C_{18}$-aryl or A, M is an alkali metal ion, alkaline earth metal ion or ammonium ion of the formula $HN(R^3)_3$, where each $R^3$, independently of the others, is hydrogen, $C_1$–$C_4$-alkyl, $C_5$–$C_{15}$-cycloalkyl, $C_6$–$C_{18}$-aryl or a group of the formula —$(CH_2)_z$—OH in which z is a number from 1 to 10, x is a number from 0 to 80 and y is a number from 0 to 50, the sum of x and y not being zero, and, to make up to 100% by weight, water and, if desired, solvents and/or additives. These oil-in-water emulsions are preferably employed in agriculture and in horticulture, in the domestic and hygiene sectors and/or in the medical sector.

18 Claims, No Drawings

OIL-IN-WATER EMULSIONS

This application is a 35 USC 371 of PCT/EP93/03165 filed Nov. 11, 1993, published as WO94/10839 May 26, 1994.

The prior art already includes oil-in-water emulsions which contain active substances from the class of the phosphates and carbamates and which are employed in agriculture, in horticulture, in the domestic and hygiene sectors, and/or in the medical sector.

U.S. Pat. No. 4,107,302 discloses aqueous emulsion concentrates (EW) which, in addition to the organophosphorus active substance, for insecticidal control, and the surfactant, additionally and compulsorily contain an aqueous buffer solution for establishing a specific pH range.

EP-B-0 196 463 describes macroemulsions containing phosphates, in which nonionic nonylphenol/propylene oxide/ethylene oxide adducts are used to disperse the active substance.

The oil-in-water emulsions known from EP-B-0 062 181 contain, in addition to the active substances, as emulsifier at least one and generally two or more alkylaryl polyglycol ethers in a mixture with ionic alkylarylsulfonic acid salts.

EP-B-0 289 909 discloses aqueous, phase-stable, homogeneous emulsion compositions of organophosphorus pesticides, which contain, in addition to the active substance, a nonionic block copolymer, random copolymer, or random/block copolymer as surfactant and urea as a thickener and stabilizer.

EP-A-0 160 182 relates to aqueous microemulsions containing, in addition to a synthetic pyrethroid as active substance, an emulsifier mixture comprising calcium dodecylbenzenesulfonate, ethoxylated distyrylphenolammonium sulfate and ethoxylated tristyrylphenol.

In the emulsion concentrates (EC) described in GB-B-0 717 279 and U.S. Pat. No. 2,696,453, the quantity in which the active substances are dissolved in organic solvents (e.g. xylene, toluene, kerosene) and admixed with an emulsifier mixture comprising a nonionic and an ionic surfactant (polyoxyalkylene glycol/alkylarylsulfonate) ensures that, when these concentrates are diluted with water to the application concentration, a sufficiently stable aqueous emulsion is formed. On account of the solvents they contain, however, the concentrates are often associated with disadvantages in respect of their combustibility, toxicological characteristics, tolerance by plants and odor.

The abovementioned aqueous emulsifiable concentrates (EW) can only be prepared using additional auxiliaries, such as a thickener, stabilizer and buffer, organic solvents, and surfactant mixtures based mostly on nonionic and ionic surfactants.

Oil-in-water emulsions in the form of aqueous emulsifiable concentrates (EW) have now been found which, in addition to active substances from the class of phosphates and/or carbamates, and water, compulsorily contain at least one salt of an aryl polyglycol ether phosphate as ionic surfactant. In this case, the use of organic solvents, nonionic/ionic surfactant mixtures and/or additional auxiliaries, such as a thickener, stabilizer and buffer, is not compulsory.

It must be referred to as extremely surprising that the aqueous emulsifiable concentrates (EW) according to the invention are stable, since, on the basis of the known prior art, it was not to be expected that such emulsions, containing no thickener, stabilizer or buffer, little or no organic solvent and only one class of surfactant, are stable over a prolonged period.

The invention relates to oil-in-water emulsions comprising 0.001–70% by weight, preferably from 0.5 to 45% by weight, of at least one active substance from the class of the phosphates and/or carbamates, from 0.001–20% by weight, preferably from 0.1–10% by weight, of at least one salt of an aryl polyglycol ether phosphate of the formula I $$\left[ (R^1)_a \underset{A}{\underset{\|}{\bigcirc}} \!-\! O-(CH_2-CH_2-O)_x\!-\!(CH-CH_2-O)_y \right] \underset{R^2}{\overset{O}{\underset{\|}{-P-O^-}}} M^+$$

in which each $R^1$, independently of the others, is hydrogen, $C_1$–$C_{24}$-alkyl, $C_5$–$C_{15}$-cycloalkyl, $C_6$–$C_{24}$-aryl or $C_6$–$C_{24}$-alkaryl, $R^2$ is hydrogen, —O—$C_1$–$C_{24}$-alkyl, —O—$C_5$–$C_{15}$-cycloalkyl, —O—$C_6$–$C_{18}$-aryl or A, M is an alkali metal ion, alkaline earth metal ion or ammonium ion of the formula $HN^{\oplus}(R^3)_3$, where each $R^3$, independently of the others, is hydrogen, $C_1$–$C_4$-alkyl, $C_5$–$C_{15}$-cycloalkyl, $C_6$–$C_{18}$-aryl or a group of the formula —$(CH_2)_z$—OH in which z is a number from 1 to 10, x is a number from 0 to 80 and y is a number from 0 to 50, the sum of x and y not being zero, and, to make up to 100% by weight, water and, if desired, solvents and/or additives.

The oil-in-water emulsions according to the invention contain at least one agrochemical active substance, an active substance for controlling pests in the domestic and hygiene sectors and/or a pharmacologically active substance from the class of the phosphates and/or carbamates. Suitable active substances include both those substances which are liquid at room temperature and those which are solid at room temperature. Such active substances are known and are described in "The Pesticide Manual", 9th edition, The British Crop Protection Council, 1991.

In the present case, the agrochemical substances are to be understood as meaning all active substances which can usually be used in crop protection. These include, for example, insecticides, acaricides, nematicides, fungicides, herbicides, growth regulators and fertilizers.

Specific examples of such active substances are:

O,O-Diethyl O-[2-isopropyl-4-methyl-6-pyrimidinyl] thiophosphate (diazinon)

O,O-Diethyl O-[3,5,6-trichloro-2-pyridyl]thiophosphate (chlorpyrophos)

2-(1-Methylpropyl)phenyl methylcarbamate (BPMC)

O,O-dimethyl S-methylcarbamoylmethyl thiophosphate (dimethoate)

Chlorobicyclo[3.2.0]hepta-2,6-dien-6-yl phosphate (heptenophos)

O,O-Diethyl O-1-phenyl-1H-1,2,4-triazol-3-yl thiophosphate (triazophos)

Ethyl 2-diethoxyphosphinothioyloxy-5-methylpyrazolyl[1,5-α]pyrimidine-6-carboxylate (pyrazophos)

O,O-Diethyl O-(4-nitrophenyl) thionophosphonate

O,O-Dimethyl O-(4-nitrophenyl) thionophsophate (fenitrothion)

O-Ethyl O-4-methylthiophenyl S-propyldithiophosphate

2-Isopropoxyphenyl N-methylcarbamate 2,3-Dihydro-2,2-dimethyl-7-benzofuryl methylcarbamate 3,5-Dimethyl-4-methylthiophenyl N-methylcarbamate O,O-Diethyl O-(3-chloro-4-methyl-7-coumarinyl) thiophosphate S-[1,2-bis(ethoxycarbonyl)ethyl]O,O-dimethyl dithiophosphate (malathion)

O,O-Dimethyl O-4-methylmercapto-3-methylphenyl thionophosphate (fenthion, Lebaycid)

O-Ethyl O-2-isopropyloxycarbonylphenyl N-isopropylthionophosphoramide.

In the present case, active substances for controlling pests in the domestic and hygiene sectors are to be understood as all conventional active substances of low solubility in water. Specific examples of such active substances are:

2-Isopropoxyphenyl N-methylcarbamate

O,O-Diethyl-O-4-nitrophenyl thionophosphate (ethylparathion)

O,O-Dimethyl O-4-nitrophenyl thionophosphate (methylparathion)

S-[1,2-bis(Ethoxycarbonyl)ethyl]O,O-dimethyl dithiophosphate

O,O-Dimethyl O-3-methyl-4-nitrophenyl thionophosphate (sumithion, folithion)

O,O-Dimethyl O-4-methylmercapto-3-methylphenyl thionophosphate (Lebaycid, fenthion).

In the present case, pharmacologically active substances are to be understood as substances of low solubility in water which can preferably be employed in the veterinary sector. An example of such active substances is chlorobicyclo [3.2.0]hepta-2,6-dien-6-yl phosphate (heptenophos).

The oil-in-water emulsions according to the invention contain at least one salt of an aryl polyglycol ether phosphate of the formula I $$\left[ (R^1)_3 \underset{A}{\underset{|}{\bigcirc}} -O-(CH_2-CH_2-O)_x-(CH-CH_2-O)_y \right] \underset{R^2}{\overset{O}{\underset{|}{-P-O^-}}} M^+$$

in which $R^1$, $R^2$, M, x and y have the aforementioned meaning.

The radicals $R^1$, $R^2$ and $R^3$ may be substituted. Suitable substituents are halogens such as bromine and chlorine, hydroxyl, nitro, amino, carboxyl and sulfo or their ester group. Preferred compounds of this type are those in which $R^1$ is $C_1-C_6$-alkyl, phenyl, naphthyl, diphenyl, styryl or 1-phenylethyl, $R^2$ is $C_1-C_6$-alkyl, phenyl or A, M is an alkali metal ion, a mono-, di- or triethylammonium ion or a triethanolammonium ion, x is a number from 10 to 50, and y is a number from 10 to 35.

Particularly preferred surfactants are potassium or triethylammonium 2,4,6-tris(1-phenylethyl)phenol polyglycol ether monophosphate containing on average 20 EO units (EO=ethylene oxide), and triethanolamine salts of a mixture of mono- and diphosphates of a tristyrylphenol polyglycol ether containing on average from 18 to 20 EO units.

The surfactants of the formula I are known but have previously been employed in formulations in combination with other surfactants. In this context, reference is made to the following publications: EP-A-0 163 598, EP-A-0 201 417, EP-A-0 364 328, EP-A-0 432 061, EP-A-0 432 062, DE-A-3 503 706, DE-A-3 542 440, DE-A-3 614 788 and DE-A-3 624 910.

The oil-in-water emulsions contain water as the continuous phase. Where concentrates are concerned, the amount of water is relatively low. In the case of heavily diluted emulsions, considerable quantities of water are present. The oil phase (=disperse phase) is distributed in the form of droplets in the aqueous phase. The size of the oil droplets can in this case be varied within a certain range. In general, the particle diameter is between 0.01 and 10 μm, preferably between 0.2 and 5.0 μm. In the oil-in-water emulsions according to the invention, the percentage proportions of the components they contain can be varied within relatively large ranges. The proportion of active substances from the class of the phosphates and/or carbamates is in general between 0.001 and 70% by weight, preferably between 0.5 and 45% by weight. The proportion of surfactant of the formula I is in general from 0.001 to 20% by weight, preferably from 0.1 to 10% by weight.

Furthermore, these oil-in-water emulsions contain only a very small quantity of organic solvents, or even none at all. They are therefore not combustible, are virtually or totally free of the odor problems caused by organic solvents, and in general have a lower toxicity and phytotoxicity than corresponding formulations which contain organic solvents at the concentrations which are otherwise usual. Suitable organic solvents which they may, if appropriate, contain are all conventional organic solvents or solvent mixtures which are of low miscibility with water and which boil at between 100° C. and 290° C. Preferred such solvents are aromatic hydrocarbons such as xylene, toluene, ethylbenzene, alkylated benzenes containing on average 9 carbon atoms, such as the solvent grades known under the name Solvesso® (Esso Chemic GmbH) and dimethylnaphthalene, and halogenated aromatic hydrocarbons such as chlorobenzenes, aliphatic hydrocarbons such as benzine and petroleum ether, cycloaliphatic hydrocarbons such as cyclohexane, and alcohols and ketones, such as n-butanol, n-hexanol, iso-hexanol, n-octanol, cyclohexanol, benzyl alcohol and di-n-butyl ketone, and also ethers and esters.

The content of organic solvents is in general from 0–50% by weight, preferably from 0–20% by weight, based on the emulsion.

Additives which the oil-in-water emulsions according to the invention may suitably contain are preservatives, antifreezes, dyes and odor-improvers.

Examples of preservatives are 2-hydroxybiphenyl, sorbic acid, p-hydroxybenzaldehyde, methyl p-hydroxybenzoate, benzaldehyde, benzoic acid, propyl p-hydroxybenzoate and p-nitrophenol. The content of preservative in the emulsion is between 0.01 and 1% by weight.

Suitable antifreezes are glycol, glycerol, polyethylene glycol, sugar and salts such as ammonium sulfate and sodium oleate, of which the emulsions usually contain from 1 to 10% by weight.

Examples of dyes which may be mentioned are azo dyes and phthalocyanine dyes. Perfume oils can be employed as odor-improvers.

An appropriate preparation process is described in EP-B-0 130 370.

In addition to the advantages already mentioned in connection with the low content of organic solvents, the oil-in-water emulsions are also notable for their stability under practical conditions. On long term storage both at high temperatures (50° C.) and at low temperatures (−5° C., −10° C.), these emulsions remain unchanged with respect to their physical stability and their content of active substance. An additional advantage is that active substances can be emulsified equally well whether they are solid or liquid at room temperature.

The oil-in-water emulsions according to the invention can be applied either as formulated or after previous dilution. The application rate depends on the concentration of the oil-in-water emulsion and on the particular indication.

The emulsions are applied by the conventional methods; that is, for example, by spraying or pouring.

The formulation examples given in the following Tables are evidence of the broad range of application. ®Solvesso 150 (Esso Chemie GmbH): boiling range 186°–205° C., aromatic content 99%.

Surfactant 1: triethanolamine salt of a mixture of mono- and diphosphates of 2,4,6-tris(1-phenylethyl)phenol polyglycol ether containing on average 20 EO units.

Surfactant 2: triethanolamine salt of the monophosphate of 2,4,6-tris(1-phenylethyl)phenol polyglycol ether containing on average 20 EO units.

Surfactant 3: tristyrylphenol containing on average 20–26 EO units.

Table 1 shows oil-in-water emulsions according to the invention which are stable over a period of at least three months (storage temperature: 25° C.; 50° C.).

Table 2 shows, as comparative examples, oil-in-water emulsions containing a nonionic surfactant (tristyrylphenol containing 20 mol of EO) and an ionic surfactant (calcium phenylsulfonate). In these emulsions, the active substance is substantially broken down (>10% by weight) after only 2 weeks (storage temperature: 25° C.; 50° C.).

0.001–70% by weight of at least one liquid active substance, said active substance being a phosphate or carbamate or mixture thereof;

from 0.001–20% by weight, of emulsifier consisting essentially of at least one salt of an aryl polyglycol ether phosphate of the formula I

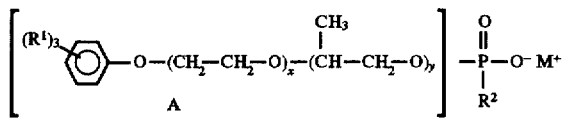

in which
each $R^1$, independently of the others, is an unsubstituted or substituted
$C_1$–$C_{24}$-alkyl, $C_5$–$C_{15}$-cycloalkyl, $C_8$–$C_{24}$-aryl or $C_6$–$C_{24}$-alkaryl group;

TABLE 1

| Examples; components in % by weight; water to 100% by weight | | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 | 13 |
| Surfactant 1 | | 7 | 5 | | | | 5 | | | | | | |
| Surfactant 2 | 7 | | | 10 | 7 | 4 | | 5 | 7 | 10 | 5 | 3 | 3 |
| Xylene | 20 | 20 | 10 | | 20 | 20 | 20 | 20 | 20 | 20 | 20 | 20 | 20 |
| ® Solvesso 150 | | | 10 | | | | | | | | | | |
| Malathion | 42 | 42 | 42 | 42 | | | | | | | | | |
| Ethyl-parathion | | | | | 51 | 51 | 51 | 51 | | | | | |
| Fenitrothion | | | | | | | | | | | 41.7 | 42 | 52 |
| Diazinon | | | | | | | | | | | | 52 | 52 |
| Temperature stability | −5 to 50° C. | −5 to 50° C. | −5 to 50° C. | −5 to 50° C. | −5 to 50° C. | −5 to 50° C. | −5 to 50° C. | −5 to 50° C. | −5 to 50° C. | −5 to 50° C. | −5 to 50° C. | −5 to 50° C. | −5 to 50° C. |

| Examples; in % by weight; water to 100% by weight | | | | | | | | | | | |
|---|---|---|---|---|---|---|---|---|---|---|---|
| | 14 | 15 | 16 | 17 | 18 | 19 | 20 | 21 | 22 | 23 | 24 |
| Surfactant 1 | | | | | | | 7 | 7 | 7 | 7 | 7 |
| Surfactant 2 | 7 | 7 | 4 | 3 | 7 | 5 | | | | | |
| Xylene | 35 | 35 | 20 | 20 | 20 | 10 | 18 | 32 | 5 | 20 | 26 |
| ® Solvesso 150 | | | | | | 10 | | | | | |
| Malathion | | | | | | | | | | 42 | |
| Chlorpyrophos | 24 | 24 | | | | | | | | | |
| Fenthion | | | 52.4 | 52.4 | | | | | | | |
| BPMC | | | | | 50 | 50 | | | | | |
| Heptenophos | | | | | | | | | 54 | | |
| Triazophos | | | | | | | | | | | 40 |
| Pyrazophos | | | | | | | 15 | 26 | | | |
| Antifreeze | | | | | | | 10 | 10 | 10 | | 10 |
| Temperature stability | −5 to 45° C. | −5 to 45° C. | −5 to 50° C. | −5 to 50° C. | −5 to 40° C. | −10 to 40° C. | −10 to 50° C. | −10 to 50° C. | −10 to 40° C. | −5 to 50° C. | −10 to 40° C. |

TABLE 2

| | Examples; % by weight; water to 100% by weight | | | |
|---|---|---|---|---|
| Composition | V1 | V2 | V3 | V4 |
| Surfactant 3 | | | 7.5 | |
| ® Emulsogen EL 400 | 8 | 7 | | |
| Ca phenylsulfonate | 4 | 4 | 1.5 | 11.2 |
| ® Emulsogen 3510 | | | | 13.8 |
| Xylene | 20 | 20 | | |
| Malathion | | | | 52.6 |
| Diazinon | | | 61.7 | |
| Heptenophos | 30 | 25 | | |
| Temperature stability | ./. | ./. | ./. | ./. |

We claim:
1. An oil-in-water emulsion comprising

$R^2$ is hydrogen or is an unsubstituted or substituted —O—$C_1$–$C_{24}$-alkyl, —O—$C_5$–$C_{15}$-cycloalkyl, —O—$C_6$–$C_{18}$-aryl or A group, where A is the A group of said formula I, M is an alkali metal ion, alkaline earth metal ion or ammonium ion of the formula $HN(R^3)_3$, where each $R^3$, independently of the others, is hydrogen or is an unsubstituted or substituted $C_1$–$C_4$-alkyl, $C_5$–$C_{15}$-cycloalkyl, $C_6$–$C_{18}$-aryl, or —$(CH_2)_z$—OH group, in which z is a number from 1 to 10;

x is a number from 0 to 80 and y is a number from 0 to 50, the sum of x and y not being zero, and sufficient water to provide an oil-in-water emulsion with an aqueous phase as the continuous phase.

2. An emulsion as claimed in claim 1, wherein said emulsion comprises, to make up 100% by weight, water and optionally at least one solvent and at least one additive.

3. An emulsion as claimed in claim 1, wherein said emulsion further comprises at least one additional active substance which is agrochemically active or is active for controlling pests.

4. An emulsion as claimed in claim 1, wherein said active substance is pharmacologically active.

5. An emulsion as claimed in claim 1, wherein the salt of an aryl polyglycol ether phosphate is a mono- or diphosphate of a phenol polyglycol ether or a mixture thereof.

6. An emulsion as claimed in claim 1, which contains from 0–50% by weight, based on the emulsion, of an organic solvent.

7. An emulsion as claimed in claim 6, wherein said organic solvent is an aromatic, aliphatic or cycloaliphatic hydrocarbon or an alcohol or ketone.

8. An emulsion as claimed in claim 6, wherein the amount of organic solvent does not exceed 20% by weight, based on the emulsion.

9. An emulsion as claimed in claim 1, wherein said emulsion is essentially free of organic solvent.

10. An emulsion as claimed in claim 1, which emulsion further comprises at least one additive, said additive being a preservative, an antifreeze, an odor-improver or an acid.

11. An emulsion as claimed in claim 1, wherein the oil phase of the oil-in-water emulsion is distributed in said aqueous phase in the form of drops having an average particle diameter of between 0.01 and 10 µm.

12. An emulsion as claimed in claim 11, wherein said average particle diameter is in the range of 0.2 to 0.5 µm.

13. An emulsion as claimed in claim 1, wherein the emulsion consists essentially of:

0.5 to 45% by weight of a said active substance, 0.1–10% by weight of at least one said salt of an aryl polyglycol ether phosphate, and to make up 100% by weight, water and, optionally, at least one additive or solvent;

said emulsion being essentially free of any thickener, stabilizer, or buffer.

14. A method for treating plants comprising the step of applying to said plants an emulsion as claimed in claim 1.

15. A method for controlling pests comprising the step of treating the pests with an emulsion as claimed in claim 1.

16. An oil-in-water emulsion comprising 0.001–70% by weight of at least one liquid active substance, said active substance being a phosphate or a carbamate or a mixture thereof, sufficient water to form said oil-in-water emulsion, from 0.001–20% by weight, of at least one salt of an aryl polyglycol ether phosphate of the formula I

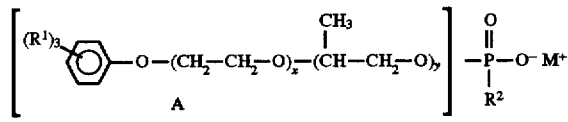

in which

A represents the radical set forth within the brackets in the foregoing formula I, each $R^1$, independently of the others, is $C_1$–$C_{24}$-alkyl, $C_5$–$C_{15}$-cycloalkyl, $C_8$–$C_{24}$-aryl or $C_6$–$C_{24}$-alkaryl, $R^2$ is hydrogen, —O—$C_1$–$C_{24}$-alkyl, —O—$C_5$–$C_{15}$-cycloalkyl, —O—$C_6$–$C_{18}$-aryl or A, M is an alkali metal ion, alkaline earth metal ion or ammonium ion of the formula $HN(R^3)_3$, where each $R^3$, independently of the others, is hydrogen, $C_1$–$C_4$-alkyl, $C_5$–$C_{15}$-cycloalkyl, $C_6$–$C_{18}$-aryl, or a group of the formula —$(CH_2)_z$—OH in which z is a number from 1 to 10;

x is a number from 0 to 80, and y is a number from 0 to 50, the sum of x and y not being zero.

17. An emulsion as claimed in claim 16, wherein said emulsion comprises, to make up 100% by weight, water and optionally at least one solvent and at least one additive.

18. An emulsion as claimed in claim 1, wherein said emulsion further comprises at least one additional active substance which is agrochemically or pharmacologically active or is active for controlling pests.

* * * * *